US011559521B2

(12) United States Patent
Worthington

(10) Patent No.: US 11,559,521 B2
(45) Date of Patent: Jan. 24, 2023

(54) ANALGESIC FORMULATIONS AND METHODS FOR REDUCED POSTOPERATIVE NAUSEA AND VOMITING AND ENHANCED POSTOPERATIVE PAIN RELIEF

(71) Applicant: William Bradley Worthington, Nashville, TN (US)

(72) Inventor: William Bradley Worthington, Nashville, TN (US)

( * ) Notice: Subject to any disclaimer, the term of this patent is extended or adjusted under 35 U.S.C. 154(b) by 18 days.

(21) Appl. No.: 16/834,863

(22) Filed: Mar. 30, 2020

(65) Prior Publication Data

US 2020/0230120 A1 Jul. 23, 2020

Related U.S. Application Data

(63) Continuation-in-part of application No. 16/129,126, filed on Sep. 12, 2018, now abandoned, which is a continuation of application No. 14/997,046, filed on Jan. 15, 2016, now Pat. No. 10,098,872, which is a continuation-in-part of application No. 14/337,819, filed on Jul. 22, 2014, now abandoned.

(60) Provisional application No. 61/856,979, filed on Jul. 22, 2013.

(51) Int. Cl.
| | | |
|---|---|---|
| *A61K 31/135* | (2006.01) | |
| *A61P 23/02* | (2006.01) | |
| *A61K 31/445* | (2006.01) | |
| *A61M 25/00* | (2006.01) | |
| *A61K 31/407* | (2006.01) | |
| *A61P 29/00* | (2006.01) | |

(52) U.S. Cl.
CPC .......... *A61K 31/445* (2013.01); *A61K 31/135* (2013.01); *A61K 31/407* (2013.01); *A61M 25/0068* (2013.01); *A61K 2300/00* (2013.01); *A61P 23/02* (2018.01); *A61P 29/00* (2018.01)

(58) Field of Classification Search
CPC ...... A61P 23/02; A61P 29/00; A61K 2300/00; A61K 31/135; A61K 31/407; A61K 31/445
See application file for complete search history.

(56) References Cited

U.S. PATENT DOCUMENTS

| 8,992,951 B2 | 3/2015 | Henry |
| 2004/0265364 A1 | 12/2004 | Ozturk et al. |

FOREIGN PATENT DOCUMENTS

| EP | 0799051 B1 | 7/2004 | |
| WO | WO2012054831 A2 | 4/2012 | |
| WO | WO-2012054831 A2 * | 4/2012 | ........... A61K 31/407 |

OTHER PUBLICATIONS

Misiolek et al, Anaesthesiology Intensive Therapy 2014, vol. 46, No. 4, 221-244 (Year: 2014).*
Patel et al. Comparative study of bupivacaine vs bupivacaine and ketamine (intrathecally) during intraoperative and post operative analgesia in non PIH caesarian section. National Journal of Medical Research. vol. 1 Issue 2 Oct.-Dec. 2011 ISSN 2249-4995. pp. 71-75 (Year: 2011).*
Sveticic et al. Combinations of morphine with ketamine for patient-controlled analgesia: A new optimization method. Anesthesiology (Hagerstwon) May 2003 vol. 98. No. 5, pp. 1195-1205.
Wukovits et al. Similar analgesic effect after popliteal fossa nerve blockade with 0.375% and 0.75% bupivacaine. HSS journal: the musculoskeletal journal of Hospital for Special Surgery, (Sep. 2007.) vol. 3 No. 2 pp. 173-176.
Patel et al. Comparative study of bupivacaine vs bupivacaine and ketamine (intrathecally) during intraoperative and post operative analgesia in non PIH caesarian section. National Journal of Medical Research. vol. 1 Issue 2 Oct.-Dec. 2011 ISSN 2249-4995. pp. 71-75.
Sébastien P. et al. Nausea and vomiting after surgery. Continuing Education In Anesthesia Critical Care and Pain 2013, 13 (1), 28-32.
Gan T. J. et al. Consensus Guidelines for the Management of Postoperative Nausea and Vomiting. Anesthesia & Analgesia 2014; 118:85-113.
Koivuranta M. et al. A survey of postoperative nausea and vomiting. Anesthesia, 1997, 443-449.
Shaikh S. et al. Pain, nausea, vomiting and ocular complications delay discharge following ambulatory microdiscectomy. Canadian Journal of Anesthesia 2003, 50(5), 514-518.
Cruthirds D. et al. Review and recommendations for the prevention, management, and treatment of postoperative and post discharge nausea and vomiting. Oral and Maxillofacial Surgery 2013, 115(5), 601-611.
Bion J. F. et al. Intrathecal ketamine for war surgery. A preliminary study under field conditions. Anesthesia, 1984, 39 (10), 1023-1028, The Association of Anesthetists of Gt Britain and Ireland.

(Continued)

*Primary Examiner* — Craig D Ricci
*Assistant Examiner* — Janet L Coppins
(74) *Attorney, Agent, or Firm* — Nguyen Tarbet LLC

(57) ABSTRACT

A multimodal anti-emetic anesthetic/analgesic formulation for pain control not limited to postoperative pain control is described herein. The opioid-free/sparing anesthetic/analgesic formulation comprises a local anesthetic, an N-methyl-D-aspartate (NMDA) receptor antagonist, and a cyclooxygenase (COX) inhibitor such as Bupivacaine Hydrochloride, Ketamine Hydrochloride, and Ketorolac Tromethamine, which is effective to significantly reduce postoperative nausea and vomiting and enhance postoperative pain relief as compared to existing prior art anesthetics/analgesics. The formulation is administered to a mammal in need of anesthesia/analgesia and can be used as a preemptive and preventative multimodal analgesic. The formulation may have a buffer to enhance its shelf life and improve pharmacokinetics. The formulation may further comprise an alpha agonist, a steroid, a Transient Receptor Potential Channel agonist or antagonist, a beta-lactam antibiotic, a protein kinase inhibitor, a competitive or non-competitive glycine or glutamate antagonist, a glutamate or glycine inhibitor, a cyclooxygenase 3 inhibitor, or combinations thereof.

16 Claims, No Drawings

(56) References Cited

OTHER PUBLICATIONS

Kathirvel S. et al. Effects of intrathecal ketamine added to bupivacaine for spinal anaesthesia. Anesthesia, 2000, 55(9), 899-910.
Apfelbaum, J. et al. Postoperative Pain Experience: Results from a National Survey Suggest Postoperative Pair Continues to Be Undermanaged. Anesthesia Analgesia, 2003, 97:534-40.
Gan T. J, et al. Incidence, patient satisfaction and perceptions of post-surgical pain:results from a US national survey. Current Medical Research and Opinion 2014, 30(1), 149-160.
Wang L. et.al. Intrathecal ketorolac does not improve acute or chronic pain after hip arthroplasty: a randomized controlled trial. Journal of Anesthesia 2014 28:790-793.
Rahmanian A. et al. The Effects of Bupivacaine on Postoperative Back Pain After Lumbar Laminectomy: A Randomized Clinical Trial. Neurosurgery Quarterly 2014: Nov. 6, 1-5.
pk-Beyond Cosmetic Surgery; http://dririedberg.com/testimonials/pk-beyond-cosmetic-surgery.html; 2011.
Leblanc et al. Evaluation of continuous infusion of 0.5% bupivaciane by elastomeric pump for postoperative pain management after open inguinal hernia repair. J Am Coli Surg, vol. 200 No. 2 Feb. 2005 p. 198-202.
Brockway et al. Comparison of Extradural Ropivacaine and Bupivacaine British Journal of Anaesthesia 1991; 66: 31-37.
Ya Deau JT, Wukovits BU, Lasala VR, Jules-Elysée KM, Paroli L, Kahn RL, Levine DS, Lipnitsky JY, Similar Analgesic Effect After Popliteal Fossa Nerve Blockade with 0.375% and 0.75% bupivacaine. HSS J. Sep. 2007;3(2):173-6. doi: 10.1007/s11420-007-9052-5. PMID: 18751790; PMCID: PMC2504269.
Worthington, Memorandum: Experimental Use Exception & Non-Obviousness; Jan. 22, 2018.
Worthington, Analgesic Formulations and Methods for Reduced Postoperative Nausea and Vomiting and Enhanced Postoperative Pain Relief; 2018.
Worthington, Tables 1. Patel prior art Study PONV, Table 2. Wang and Rahmanian prior arts Study in Pain Relief, Table 3. Worthington prior art in Pain Relief; 2018.

\* cited by examiner

ANALGESIC FORMULATIONS AND METHODS FOR REDUCED POSTOPERATIVE NAUSEA AND VOMITING AND ENHANCED POSTOPERATIVE PAIN RELIEF

CROSS REFERENCE

This application claims priority to and is a continuation-in-part of U.S. Non-Provisional application Ser. No. 16/129,026, filed Sep. 12, 2018, which is a continuation of U.S. Non-Provisional application Ser. No. 14/997,046, filed Jan. 15, 2016, now U.S. Pat. No. 10,098,872, issued Oct. 16, 2018, which is a continuation-in-part of U.S. Non-Provisional application Ser. No. 14/337,819, filed Jul. 22, 2014, and claims priority to U.S. Provisional Patent Application No. 61/856,979, filed Jul. 22, 2013, the specification(s) of which is/are incorporated herein in their entirety by reference.

FIELD OF THE INVENTION

The present invention relates to a multimodal non-opioid analgesic formulation for pain management and anti-emesis, not limited to postoperative pain control.

BACKGROUND OF THE INVENTION

The treatment and relief of pain is one of the most common reasons patients seek medical evaluation. Pain has been defined by the International Association for the Study of Pain as the response to real or perceived tissue trauma. The word "pain" derives from the Latin "poena," or punish. Postoperative pain is an example of acute pain. During the intraoperative period, clinicians focus attention on helping abolish pain and discomfort associated with noxious stimuli and associated surgical tissue trauma. It is now recognized that many current modalities used to treat acute postoperative pain are incomplete and/or cause significant treatment related conditions. The current opioid crisis is an example where opioids used for unimodal post-operative pain give rise to significant immediate and chronic opioid related adverse effects, morbidity, and mortality.

Surgical pain causes a generalized and biphasic response. The first response due to direct surgical trauma produces transduction of nociceptive input via c-fiber and a-delta neuronal activation leading to transmission, modulation and perception of pain signals in the peripheral and central nervous system. At the time of surgical trauma, complex inflammatory processes are triggered, leading to further afferent noxious input, causing peripheral and secondary central nociceptive sensitization. This results in a reduction in the stimulation threshold of surrounding nociceptors with increased excitation and recruitment of nociceptive afferents known as wind up neuroplasticity.

Surgical trauma results in a complex local release of inflammatory mediators further contributing to peripheral sensitization and recruitment of higher threshold nociceptors, giving rise to secondary hyperalgesia; where non-painful stimuli like light touch is perceived as painful.

Central sensitization refers to processes occurring at the spinal dorsal root ganglion, dorsal horn, and higher regions of the central nervous system in response to ongoing afferent nociceptor barrage. This leads to an expansion of the nociceptive field size, increased and magnified response to nociceptive stimuli, and a reduction in the afferent stimuli threshold that is perceived as painful.

In some aspects disclosed herein, the present invention discloses a multimodal opioid-free analgesic formulation that is opioid-free/sparing comprising Bupivacaine hydrochloride, Ketamine hydrochloride, and Ketorolac tromethamine which is effective to significantly reduce postoperative nausea and vomiting and enhance postoperative pain relief as compared to existing prior art anesthetics/analgesics. Without wishing to limit the present invention to any theory or mechanism, it is believed that the formulations of the present invention are advantageous because they feature drugs that, in synergism, provide long-lasting effects that are opioid-free and anti-emetic.

Any feature, or combination of features, described herein are included within the scope of the present invention provided that the features included in any such combination are not mutually inconsistent as will be apparent from the context, this specification, and the knowledge of one of ordinary skill in the art. Additional clinical patient and patient safety advantages and unexpected innovative aspects of the present invention are apparent in the following detailed description and claims.

DESCRIPTION OF PREFERRED EMBODIMENTS

The present invention features a novel analgesic formulation and method of treating pain with said analgesic formulations. The formulations of the present invention comprise a synergistic admixture of drugs. Without wishing to limit the present invention to any theory or mechanism, it is believed that the drugs in the formulations of the present invention work together in multimodal added synergism to preemptively treat pain. The combination of the drugs provides for prolonged and effective analgesia with minimal toxicity, greater ease of use, and reduced side effects including anti-emesis. The invention is a multimodal opioid-free anti-emetic innovative admixture.

In some embodiments, the present invention discloses an opioid-free analgesic/anesthetic formulation comprising Bupivacaine hydrochloride, Ketamine hydrochloride, and Ketorolac tromethamine which is clinically effective to significantly reduce postoperative nausea and vomiting and significantly enhance postoperative pain relief as compared to existing prior art anesthetics/analgesics. The formulations of the present invention comprise a synergistic multimodal admixture of drugs. Without wishing to limit the present invention to any theory or mechanism, it is believed that the drugs in the formulations of the present invention work together in multimodal synergism to effectively treat pain and decrease nausea and vomiting. The combination of the drugs provides for prolonged and effective analgesia with minimal toxicity, greater ease of use, and reduced side effects. The invention is an opioid free anti-emetic innovation. The invention is multimodal with the individual components also demonstrating independent multimodal analgesic mechanisms of action. The invention provides an unexpected and surprising clinically significant anti-emetic benefit.

As used herein, "treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

As defined herein, an "effective amount" means the amount of a compound that, when administered to a mammal for treating a disease, is sufficient to result in such treatment for the disease. The "effective amount" will vary depending on the formulation, the disease and its severity and the age, weight, etc., of the mammal to be treated.

As defined herein, the term "agonist" refers to an admixture component that enhances a response. The agonist binds to the same site as the endogenous compound or an admixture component and produces the same type of signal, usually of equal or greater magnitude than the endogenous agent. As defined herein, the term "antagonist" refers to an admixture component that diminishes a response. The antagonist binds to the same site as the endogenous compound and diminishes or blocks the signal generated by the endogenous agent. As defined herein, the term "inhibitor" refers to an agent that slows or interferes with a chemical reaction, or a substance that reduces the activity of another substance.

As used herein, the term "admixture" refers to a mixture, mix, combination amalgamation, amalgam, union, conjunction, merging, compound, alloy, fusion, meld, composite, synthesis, homogenization, or something mixed with something else. For example, the present invention features an admixture or a combination comprising specific proportions of an anesthetic, an NMDA-receptor antagonist, and a cyclooxygenase inhibitor.

As used herein, the term "multimodal" refers to as characterized by several different modes of activity or occurrence. For example, the present invention features a formulation that provides multimodal activity comprising anesthetic, analgesic, and anti-emetic. In preferred embodiments, multimodal analgesia is defined by the use of several different drugs or drug classes, with different analgesic mechanisms of action, interfering with nociceptive neuronal transduction, transmission, modulation, and perception of pain.

As used herein, the term "formulation" refers to a material or mixture prepared according to a formula or putting together of components in appropriate relationships or structures, according to a formula. For example, the present invention features a formulation comprising specific amounts of specific compounds that collectively and independently provide multimodal mechanisms of analgesia, anti-inflammation, and anti-emesis comprising specific amounts of at least three or more compounds or drug classifications.

As used herein "NMDARA" is an NMDA (N-methyl D-aspartate) receptor antagonist (NMDARA), such as Ketamine, Trilamine, Tramadol and Dextromethorphan, Meperidine, or Minocycline, Agmatine, Magnesium, Aptiganel, or any other competitive or non-competitive N-methyl-D-aspartate receptor antagonist having analgesic activity or utility.

As used herein, a "COXi" is a cycooxygenase inhibitor, such as Ketorolac, Acetaminophen, Parecoxib, Ibuprofen, Meloxicam, Diclofenac, Ketoprofen, Celecoxib, Naproxen Sodium, Tolmetin, Etodolac, Fenoprofen, Indomethacin, Diflunisal, Nambumetone or any other parenteral drug in this class.

As defined herein, a unit of concentration represented as "1:100,000" is equivalent to 1 mg in 1 ml (or 1000 μg in 1 ml). For example, a concentration of 1% is equal to 10 mg/cc (or 10 mg/ml), 0.5% is equal to 5 mg per cc, 0.25% is equal to 2.5 mg per cc, 0.10% is equal to 1.0 mg per cc and so forth.

As used herein, postoperative nausea and vomiting (PONV) is defined as any nausea, retching, or vomiting occurring during the first 24-48 h after surgery in surgical patients[1].

It is well known in the literature that anesthetic induced postoperative nausea and vomiting (PONV) is the most common adverse drug effect in the immediate perioperative period. Gan T. J. et al.[2] and M. Koivuranta et al.[3], reported that of the patients undergoing general anesthesia, between 30% to 50% of patients suffer from PONV and this rate can increase to 80% in a high-risk subset in patients undergoing general anesthesia over a 24-hour period postoperatively. Therefore, there is still an unmet need for clinically and statistically significant enhanced methods and improvements, improving analgesia, improving or eliminating PONV compared to standard of care therapies.

In some embodiments, the formulation of the present invention comprises an admixture of three or more synergistic drugs. In preferred embodiments, this formulation is for treating pain in a mammal. As a non-limiting example, the multimodal, synergistic formulation may comprise an amide local anesthetic at about 0.01%-0.5%, an N-methyl-D-aspartate (NMDA) receptor antagonist at about 0.01-3.0 mg/cc, and a cyclooxygenase (COX) inhibitor at about 0.01-1.2 mg/cc. In other embodiments, the formulation further comprises an alpha-2-central agonist (alpha agonist), a steroid, a transient receptor potential vanilloid (TRPV) receptor antagonist or agonist, an antibiotic, a protein kinase inhibitor, a competitive or non-competitive glycine or glutamate antagonist, glutamate or glycine inhibitor, a cyclooxygenase 3 inhibitor (acetaminophen), an antifibrinolytic, or combinations thereof.

The present invention further features a method of treating pain, reducing exposure to opioids, and reducing nausea and vomiting in a subject in need of such treatment, said method comprising administering an effective amount of a formulation to a mammal in need of such treatment, the formulation comprising about 0.01%-0.5% of a local anesthetic, about 0.01-3.0 mg/cc of an N-methyl-D-aspartate (NMDA) receptor antagonist, and about 0.01-1.2 mg/cc of a cyclooxygenase (COX) inhibitor.

In other embodiments, the present invention also features a method of treating post-surgical pain in a patient in need thereof comprising administering to the patient a therapeutically effective amount of a neurokinin-1 (NK-1) receptor antagonist in combination with a pain medication.

According to some embodiments, the present invention discloses a multimodal opioid-free analgesic/anesthetic formulation comprising Bupivacaine Hydrochloride, Ketamine Hydrochloride, and Ketorolac Tromethamine at a concentration of 0.01% to 0.5%, 0.01 to 3 mg/ml, and 0.01 to 1.2 mg/ml, respectively (hereinafter "BKK Formulation") which is much more efficacious in reducing PONV when compared to prior art anesthetics/analgesics.

In some embodiments, the local anesthetic comprises Bupivacaine Hydrochloride. In some embodiments, the local anesthetic comprises Lidocaine, Ropivacaine, Levobupivacaine, Prilocaine, Amethocaine, Procaine, Cinchocaine, Mepivacaine, Etidocaine, Tetracaine or any other long or short acting local anesthetic, including ester-based local anesthetics and amide-based local anesthetics. In some embodiments, the NMDA receptor antagonist comprises Ketamine, Trilamine, Tramadol, Dextromethorphan, Meperidine, Minocycline, Agmatine, Magnesium Sulfate, Aptiganel or any other analgesic or anesthetic phencyclidine derivative having NMDA receptor antagonistic activity. In some embodiments, the COX inhibitor comprises Ketorolac, Acetaminophen, Parecoxib, Ibuprofen, Meloxicam, Diclofenac, Ketoprofen, Celecoxib, or any other parental drug in this class.

In some embodiments, the concentration of Bupivacaine Hydrochloride, Ropivacaine Hydrochloride, or Levobupivacaine Hydrochloride is about 0.125%. In some embodiments, the concentration of Bupivacaine, Ropivacaine, or Levobupivacaine is between about 0.01% to 0.05%. In some embodiments, the concentration of Bupivacaine, Ropivacaine, or Levobupivacaine is between about 0.025% to 0.075%. In some embodiments, the concentration of Bupivacaine, Ropivacaine, or Levobupivacaine is between about 0.05% to 0.1%. In some embodiments, the concentration of Bupivacaine, Ropivacaine, or Levobupivacaine is between about 0.05% to 0.125%. In some embodiments, the concentration of Bupivacaine, Ropivacaine, or Levobupivacaine is between about 0.1% to 0.15%. In some embodiments, the concentration of Bupivacaine, Ropivacaine, or Levobupivacaine is between about 0.1% to 0.2%. In some embodiments, the concentration of Bupivacaine, Ropivacaine, or Levobupivacaine is between about 0.125% to 0.2%. In some embodiments, the concentration of Bupivacaine, Ropivacaine, or Levobupivacaine is between about 0.15% to 0.25%. In some embodiments, the concentration of Bupivacaine, Ropivacaine, or Levobupivacaine is between about 0.2% to 0.3%. In some embodiments, the concentration of Bupivacaine, Ropivacaine, or Levobupivacaine is between about 0.3% to 0.4%. In some embodiments, the concentration of Bupivacaine, Ropivacaine, or Levobupivacaine is more than about 0.4%. In some embodiments, the concentration of Bupivacaine, Ropivacaine, or Levobupivacaine is more than about 0.5%. A student of the amide local anesthetic art will realize the current useful amide local anesthetics in clinically efficacious concentrations would be interchangeable in an exemplary analgesic admixture.

In some embodiments, the concentration of Ketamine is about 1 mg/ml. In some embodiments, the concentration of Ketamine is between about 0.1 to 0.5 mg/ml. In some embodiments, the concentration of Ketamine is between about 0.5 to 1.0 mg/ml. In some embodiments, the concentration of Ketamine is between about 0.5 to 1.5 mg/ml. In some embodiments, the concentration of Ketamine is between about 1 to 2 mg/ml. In some embodiments, the concentration of Ketamine is between about 1 to 3 mg/ml. In some embodiments, the concentration of Ketamine is more than 3 mg/ml and may exceed 10 mg/mi. A student of the NMDA receptor antagonist art will realize the interchangeable drug in the same class at clinically useful dosages would enhance the non-opioid actions of an exemplary opioid free multimodal analgesic and anti-emetic admixture.

In some embodiments, the concentration of Ketorolac Tromethamine is about 0.2 mg/mi. In some embodiments, the concentration of Ketorolac is between about 0.01 to 1.0 mg/ml. In some embodiments, the concentration of Ketorolac is between about 0.05 to 0.95 mg/ml. In some embodiments, the concentration of Ketorolac is between about 0.15 to 0.95 mg/mi. In some embodiments, the concentration of Ketorolac is between about 0.1 to 0.2 mg/mi. In some embodiments, the concentration of Ketorolac is between about 0.2 to 0.3 mg/mi. In some embodiments, the concentration of Ketorolac about 0.3 to 1.0 mg/ml. In some embodiments the concentration of Ketorolac is greater than 1 mg/ml. In some embodiments the concentration of Parecoxib, Diclofenac, Ibuprofen, or any other parenteral cyclooxygenase inhibitor is similar to the clinically effective Ketorolac concentration. A student of the parenteral cyclooxygenase art will understand the interchange or addition of a COX inhibitor other than Ketorolac would provide a similar analgesic effect when combined with the other classes of analgesics in the exemplary multimodal opioid free analgesic formulation.

Some aspects of the invention comprise at least a local anesthetic, a NMDA receptor antagonist, and a COX inhibitor. The local anesthetic, NMDA receptor antagonist, and COX inhibitor may be packaged as single composition to be marketed as a unit dose, or they may be packaged as two, three, or more separate compositions to be combined or admixed prior to use, e.g. translocating and admixed on the surgical field. Thus, some aspects comprise three compositions packaged in three separate sterile containers, the three compositions comprising: (1) a local anesthetic composition comprising the local anesthetic in a pharmaceutical acceptable vehicle; (2) an NMDA receptor antagonist composition comprising the NMDA receptor antagonist in a pharmaceutically acceptable vehicle; and (3) a COX inhibitor composition comprising the COX inhibitor in a pharmaceutically acceptable vehicle, each of compositions 1, 2 and 3 being at a concentration such that combination of the three compositions results in an opioid-free analgesic formulation for treatment of pain. In some other aspects, the local anesthetic, NMDA receptor antagonist and COX inhibitor are formulated in a single unit dose, each at a concentration in a pharmaceutically acceptable vehicle to constitute an opioid-free analgesic formulation for treatment of pain. In some other aspects of the invention, three or more synergistic admixture compositions are formulated in a single sterile container or, four or more separate sterile containers, each at a concentration and in a pharmaceutically acceptable vehicle to constitute an opioid-free analgesic formulation for the treatment of pain without increased incidence of PONV.

Some aspects of the invention comprise at least a local anesthetic comprising Bupivacaine, a NMDA receptor antagonist, and a COX inhibitor, which may be packaged as single composition to be marketed as a unit dose, or may be packaged as two, three, or more separate compositions to be combined prior to use, e.g. in the surgical field. In some aspects in which the local anesthetic comprises Bupivacaine Hydrochloride, the NMDA receptor antagonist comprises Ketamine Hydrochloride, and the COX inhibitor comprises Ketorolac Tromethamine; the NMDA receptor antagonist comprises Trilamine, and the COX inhibitor comprises Ketorolac; the NMDA receptor antagonist comprises Tramadol, and the COX inhibitor comprises Ketorolac; the NMDA receptor antagonist comprises Dextromethorphan, and the COX inhibitor comprises Ketorolac; the NMDA receptor antagonist comprises Meperidine, and the COX inhibitor comprises Ketorolac; the NMDA receptor antagonist comprises Minocycline, and the COX inhibitor comprises Ketorolac; the NMDA receptor antagonist comprises Agmatine, and the COX inhibitor comprises Ketorolac; the NMDA receptor antagonist comprises Magnesium Sulfate, and the COX inhibitor comprises Ketorolac; the NMDA receptor antagonist comprises Aptiganel, and the COX inhibitor comprises Ketorolac; the NMDA receptor antagonist comprises Ketamine, and the COX inhibitor comprises Acetaminophen; the NMDA receptor antagonist comprises Trilamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine, and the COX inhibitor comprises Parecoxib; the NMDA receptor antagonist comprises Trilamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine, and the COX inhibitor comprises Ibuprofen; the NMDA receptor antagonist comprises Trilamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine, and the COX inhibitor comprises Meloxicam; the NMDA receptor antagonist comprises Trilamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine, and the COX inhibitor comprises Diclofenac; the NMDA receptor antagonist comprises Trilamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Didofenac; the NMDA receptor antagonist comprises Meperidine, and the COX inhibitor comprises Diclofenac; the NMDA receptor antagonist comprises Minocycline, and the COX inhibitor comprises Diclofenac; the NMDA receptor antagonist comprises Agmatine, and the COX inhibitor comprises Diclofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine, and the COX inhibitor comprises Ketoprofen; the NMDA receptor antagonist comprises Trilamine, and the COX inhibitor comprises Ketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen; the NMDA receptor antagonist comprises Meperidine, and the COX inhibitor comprises Ketoprofen; the NMDA receptor antagonist comprises Minocycline, and the COX inhibitor comprises Ketoprofen; the NMDA receptor antagonist comprises Agmatine, and the COX inhibitor comprises Ketoprofen; the NMDA receptor antagonist comprises Magnesium Sulfate, and the COX inhibitor comprises Ketoprofen; the NMDA receptor antagonist comprises Aptiganel, and the COX inhibitor comprises Ketoprofen; the NMDA receptor antagonist comprises Ketamine, and the COX inhibitor comprises Celecoxib; the NMDA receptor antagonist comprises Trilamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; or the NMDA receptor antagonist comprises Aptiganel, and the COX inhibitor comprises Celecoxib.

Some aspects of the invention comprise at least a local anesthetic comprising Lidocaine, an NMDA receptor antagonist, and a COX inhibitor, which may be packaged as single composition to be marketed as a unit dose, or may be packaged as two, three, or more separate compositions to be combined prior to use, e.g. in the surgical field. In some aspects the local anesthetic comprises Lidocaine and the NMDA receptor antagonist comprises Ketamine, and the COX inhibitor comprises Ketorolac; the NMDA receptor antagonist comprises Trilamine, and the COX inhibitor comprises Ketorolac; the NMDA receptor antagonist comprises Tramadol, and the COX inhibitor comprises Ketorolac; the NMDA receptor antagonist comprises Dextromethorphan, and the COX inhibitor comprises Ketorolac; the NMDA receptor antagonist comprises Meperidine, and the COX inhibitor comprises Ketorolac; the NMDA receptor antagonist comprises Minocycline, and the COX inhibitor comprises Ketorolac; the NMDA receptor antagonist comprises Agmatine, and the COX inhibitor comprises Ketorolac; the NMDA receptor antagonist comprises Magnesium Sulfate, and the COX inhibitor comprises Ketorolac; the NMDA receptor antagonist comprises Aptiganel, and the COX inhibitor comprises Ketorolac; the NMDA receptor antagonist comprises Ketamine, and the COX inhibitor comprises Acetaminophen; the NMDA receptor antagonist comprises Trilamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine, and the COX inhibitor comprises Parecoxib; the NMDA receptor antagonist comprises Trilamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine, and the COX inhibitor comprises Ibuprofen; the NMDA receptor antagonist comprises Trilamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine, and the COX inhibitor comprises Meloxicam; the NMDA receptor antagonist comprises Trilamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine, and the COX inhibitor comprises Diclofenac; the NMDA receptor antagonist comprises Trilamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Diclofenac; the NMDA receptor antagonist comprises Minocycline, and the COX inhibitor comprises Diclofenac; the NMDA receptor antagonist comprises Agmatine, and the COX inhibitor comprises Diclofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine, and the COX inhibitor comprises Ketoprofen; the NMDA receptor antagonist comprises Trilamine, and the COX inhibitor comprises Ketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen; the NMDA receptor antagonist comprises Meperidine, and the COX inhibitor comprises Ketoprofen; the NMDA receptor antagonist comprises Minocycline, and the COX inhibitor comprises Ketoprofen; the NMDA receptor antagonist comprises Agmatine, and the COX inhibitor comprises Ketoprofen; the NMDA receptor antagonist comprises Magnesium Sulfate, and the COX inhibitor comprises Ketoprofen; the NMDA receptor antagonist comprises Aptiganel, and the COX inhibitor comprises Ketoprofen; the NMDA receptor antagonist comprises Ketamine, and the COX inhibitor comprises Celecoxib; the NMDA receptor antagonist comprises Trilamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocydine, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; or the NMDA receptor antagonist comprises Aptiganel, and the COX inhibitor comprises Celecoxib.

Some aspects of the invention comprise at least a local anesthetic comprising Ropivacaine, an NMDA receptor antagonist, and a COX inhibitor, which may be packaged as single composition to be marketed as a unit dose, or may be packaged as two, three, or more separate compositions to be combined prior to use, e.g. in the surgical field. In some aspects: the local anesthetic comprises Ropivacaine and: the NMDA receptor antagonist comprises Ketamine, and the COX inhibitor comprises Ketorolac; the NMDA receptor antagonist comprises Trilamine, and the COX inhibitor comprises Ketorolac; the NMDA receptor antagonist comprises Tramadol, and the COX inhibitor comprises Ketorolac; the NMDA receptor antagonist comprises Dextromethorphan, and the COX inhibitor comprises Ketorolac; the NMDA receptor antagonist comprises Meperidine, and the COX inhibitor comprises Ketorolac; the NMDA receptor antagonist comprises Minocycline, and the COX inhibitor comprises Ketorolac; the NMDA receptor antagonist comprises Agmatine, and the COX inhibitor comprises Ketorolac; the NMDA receptor antagonist comprises Magnesium Sulfate, and the COX inhibitor comprises Ketorolac; the NMDA receptor antagonist comprises Aptiganel, and the COX inhibitor comprises Ketorolac; the NMDA receptor antagonist comprises Ketamine, and the COX inhibitor comprises Acetaminophen; the NMDA receptor antagonist comprises Trilamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine, and the COX inhibitor comprises Parecoxib; the NMDA receptor antagonist comprises Trilamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Artisanal, and the COX inhibitor comprises Parecoxib; the NMDA receptor antagonist comprises Ketamine, and the COX inhibitor comprises Ibuprofen; the NMDA receptor antagonist comprises Trilamine, and the COX inhibitor comprises Ibuprofen; the NMDA receptor antagonist comprises Tramadol, and the COX inhibitor comprises ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine, and the COX inhibitor comprises Meloxicam; the NMDA receptor antagonist comprises Trilamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine, and the COX inhibitor comprises Diclofenac; the NMDA receptor antagonist comprises Trilamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Didofenac; the NMDA receptor antagonist comprises Meperidine, and the COX inhibitor comprises Diclofenac; the NMDA receptor antagonist comprises Minocycline, and the COX inhibitor comprises Diclofenac; the NMDA receptor antagonist comprises Agmatine, and the COX inhibitor comprises Didofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine, and the COX inhibitor comprises Ketoprofen; the NMDA receptor antagonist comprises Trilamine, and the COX inhibitor comprises Ketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen; the NMDA receptor antagonist comprises Meperidine, and the COX inhibitor comprises Ketoprofen; the NMDA receptor antagonist comprises Minocycline, and the COX inhibitor comprises Ketoprofen; the NMDA receptor antagonist comprises Agmatine, and the COX inhibitor comprises Ketoprofen; the NMDA receptor antagonist comprises Magnesium Sulfate, and the COX inhibitor comprises Ketoprofen; the NMDA receptor antagonist comprises Aptiganel, and the COX inhibitor comprises Ketoprofen; the NMDA receptor antagonist comprises Ketamine, and the COX inhibitor comprises Celecoxib; the NMDA receptor antagonist comprises Trilamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; or the NMDA receptor antagonist comprises Aptiganel, and the COX inhibitor comprises Celecoxib.

Some aspects of the invention comprise at least a local anesthetic comprising Levobupivacaine, an NMDA receptor antagonist, and a COX inhibitor, which may be packaged as single composition to be marketed as a unit dose, or may be packaged as two, three, or more separate compositions to be combined prior to use, e.g. in the surgical field. In some aspects, the local anesthetic comprises Levobupivacaine and: the NMDA receptor antagonist comprises Ketamine, and the COX inhibitor comprises Ketorolac; the NMDA receptor antagonist comprises Trilamine, and the COX inhibitor comprises Ketorolac; the NMDA receptor antagonist comprises Tramadol, and the COX inhibitor comprises Ketorolac; the NMDA receptor antagonist comprises Dextromethorphan, and the COX inhibitor comprises Ketorolac; the NMDA receptor antagonist comprises Meperidine, and the COX inhibitor comprises Ketorolac; the NMDA receptor antagonist comprises Minocycline, and the COX inhibitor comprises Ketorolac; the NMDA receptor antagonist comprises Agmatine, and the COX inhibitor comprises Ketorolac; the NMDA receptor antagonist comprises Magnesium Sulfate, and the COX inhibitor comprises Ketorolac; the NMDA receptor antagonist comprises Aptiganel, and the COX inhibitor comprises Ketorolac; the NMDA receptor antagonist comprises Ketamine, and the COX inhibitor comprises Acetaminophen; the NMDA receptor antagonist comprises Trilamine, and the COX inhibitor comprises Acetaminophen; the NMDA receptor antagonist comprises Tramadol, and the COX inhibitor comprises Acetaminophen; the NMDA receptor antagonist comprises Dextrometorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine, and the COX inhibitor comprises Parecoxib; the NMDA receptor antagonist comprises Trilamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine, and the COX inhibitor comprises Ibuprofen; the NMDA receptor antagonist comprises Trilamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine, and the COX inhibitor comprises Meloxicam; the NMDA receptor antagonist comprises Trilamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine, and the COX inhibitor comprises Diclofenac; the NMDA receptor antagonist comprises Trilamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Diclofenac; the NMDA receptor antagonist comprises Minocycline, and the COX inhibitor comprises Diclofenac; the NMDA receptor antagonist comprises Agmatine, and the COX inhibitor comprises Diclofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine, and the COX inhibitor comprises Ketoprofen; the NMDA receptor antagonist comprises Trilamine, and the COX inhibitor comprises Ketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen; the NMDA receptor antagonist comprises Meperidine, and the COX inhibitor comprises Ketoprofen; the NMDA receptor antagonist comprises Minocycline, and the COX inhibitor comprises Ketoprofen; the NMDA receptor antagonist comprises Agmatine, and the COX inhibitor comprises Ketoprofen; the NMDA receptor antagonist comprises Magnesium Sulfate, and the COX inhibitor comprises Ketoprofen; the NMDA receptor antagonist comprises Aptiganel, and the COX inhibitor comprises Ketoprofen; the NMDA receptor antagonist comprises Trilamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; or the NMDA receptor antagonist comprises Aptiganel, and the COX inhibitor comprises Celecoxib.

Some aspects of the invention comprise at least a local anesthetic comprising Prilocaine, an NMDA receptor antagonist, and a COX inhibitor, which may be packaged as single composition to be marketed as a unit dose, or may be packaged as two, three, or more separate compositions to be combined prior to use, e.g. in the surgical field. In some aspects, the local anesthetic comprises Prilocaine and: the NMDA receptor antagonist comprises Ketamine, and the COX inhibitor comprises Ketorolac; the NMDA receptor antagonist comprises Trilamine, and the COX inhibitor comprises Ketorolac; the NMDA receptor antagonist comprises Tramadol, and the COX inhibitor comprises Ketorolac; the NMDA receptor antagonist comprises Dextromethorphan, and the COX inhibitor comprises Ketorolac; the NMDA receptor antagonist comprises Meperidine, and the COX inhibitor comprises Ketorolac; the NMDA receptor antagonist comprises Minocycline, and the COX inhibitor comprises Ketorolac; the NMDA receptor antagonist comprises Agmatine, and the COX inhibitor comprises Ketorolac; the NMDA receptor antagonist comprises Magnesium Sulfate, and the COX inhibitor comprises Ketorolac; the NMDA receptor antagonist comprises Aptiganel, and the COX inhibitor comprises Ketorolac; the NMDA receptor antagonist comprises Ketamine, and the COX inhibitor comprises Acetaminophen; the NMDA receptor antagonist comprises Trilamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine, and the COX inhibitor comprises Parecoxib; the NMDA receptor antagonist comprises Trilamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine, and the COX inhibitor comprises Ibuprofen; the NMDA receptor antagonist comprises Trilamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine, and the COX inhibitor comprises Meloxicam; the NMDA receptor antagonist comprises Trilamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine, and the COX inhibitor comprises Diclofenac; the NMDA receptor antagonist comprises Trilamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Diclofenac; the NMDA receptor antagonist comprises Minocydine, and the COX inhibitor comprises Diclofenac; the NMDA receptor antagonist comprises Agmatine, and the COX inhibitor comprises Diclofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine, and the COX inhibitor comprises Ketoprofen; the NMDA receptor antagonist comprises Trilamine, and the COX inhibitor comprises Ketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen; the NMDA receptor antagonist comprises Meperidine, and the COX inhibitor comprises Ketoprofen; the NMDA receptor antagonist comprises Minocycline, and the COX inhibitor comprises Ketoprofen; the NMDA receptor antagonist comprises Agmatine, and the COX inhibitor comprises Ketoprofen; the NMDA receptor antagonist comprises Magnesium Sulfate, and the COX inhibitor comprises Ketoprofen; the NMDA receptor antagonist comprises Aptiganel, and the COX inhibitor comprises Ketoprofen; the NMDA receptor antagonist comprises Ketamine, and the COX inhibitor comprises Celecoxib; the NMDA receptor antagonist comprises Trilamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; or the NMDA receptor antagonist comprises Aptiganel, and the COX inhibitor comprises Celecoxib.

Some aspects of the invention comprise at least a local anesthetic comprising Amethocaine, an NMDA receptor antagonist, and a COX inhibitor, which may be packaged as single composition to be marketed as a unit dose, or may be packaged as two, three, or more separate compositions to be combined prior to use, e.g. in the surgical field. In some embodiments, the local anesthetic comprises Amethocaine and: the NMDA receptor antagonist comprises Ketamine, and the COX inhibitor comprises Ketorolac; the NMDA receptor antagonist comprises Trilamine, and the COX inhibitor comprises Ketorolac; the NMDA receptor antagonist comprises Tramadol, and the COX inhibitor comprises Ketorolac; the NMDA receptor antagonist comprises Dextromethorphan, and the COX inhibitor comprises Ketorolac; the NMDA receptor antagonist comprises Meperidine, and the COX inhibitor comprises Ketorolac; the NMDA receptor antagonist comprises Minocycline, and the COX inhibitor comprises Ketorolac; the NMDA receptor antagonist comprises Agmatine, and the COX inhibitor comprises Ketorolac; the NMDA receptor antagonist comprises Magnesium Sulfate, and the COX inhibitor comprises ketorolac; the NMDA receptor antagonist comprises Aptiganel, and the COX inhibitor comprises Ketorolac; the NMDA receptor antagonist comprises Ketamine, and the COX inhibitor comprises Acetaminophen; the NMDA receptor antagonist comprises Trilamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine, and the COX inhibitor comprises Parecoxib; the NMDA receptor antagonist comprises Trolamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine, and the COX inhibitor comprises Ibuprofen; the NMDA receptor antagonist comprises Trilamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine, and the COX inhibitor comprises Meloxicam; the NMDA receptor antagonist comprises Trilamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine, and the COX inhibitor comprises Diclofenac; the NMDA receptor antagonist comprises Trilamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Diclofenac; the NMDA receptor antagonist comprises Minocycline, and the COX inhibitor comprises Diclofenac; the NMDA receptor antagonist comprises Agmatine, and the COX inhibitor comprises Diclofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine, and the COX inhibitor comprises Ketoprofen; the NMDA receptor antagonist comprises Trilamine, and the COX inhibitor comprises Ketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen; the NMDA receptor antagonist comprises Meperidine, and the COX inhibitor comprises Ketoprofen; the NMDA receptor antagonist comprises Minocycline, and the COX inhibitor comprises Ketoprofen; the NMDA receptor antagonist comprises Agmatine, and the COX inhibitor comprises Ketoprofen; the NMDA receptor antagonist comprises Magnesium Sulfate, and the COX inhibitor comprises Ketoprofen; the NMDA receptor antagonist comprises Aptiganel, and the COX inhibitor comprises Ketoprofen; the NMDA receptor antagonist comprises Ketamine, and the COX inhibitor comprises Celecoxib; the NMDA receptor antagonist comprises Trilamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; or the NMDA receptor antagonist comprises Aptiganel, and the COX inhibitor comprises Celecoxib.

Some aspects of the invention comprise at least a local anesthetic comprising Procaine, an NMDA receptor antagonist, and a COX inhibitor, which may be packaged as single composition to be marketed as a unit dose, or may be packaged as two, three, or more separate compositions to be combined prior to use, e.g. in the surgical field. In some aspects, the local anesthetic comprises Procaine and: the NMDA receptor antagonist comprises Ketamine, and the COX inhibitor comprises Ketorolac; the NMDA receptor antagonist comprises Trilamine, and the COX inhibitor comprises Ketorolac; the NMDA receptor antagonist comprises Tramadol, and the COX inhibitor comprises Ketorolac; the NMDA receptor antagonist comprises Dextromethorphan, and the COX inhibitor comprises Ketorolac; the NMDA receptor antagonist comprises Meperidine, and the COX inhibitor comprises Ketorolac; the NMDA receptor antagonist comprises Minocycline, and the COX inhibitor comprises Ketorolac; the NMDA receptor antagonist comprises Agmatine, and the COX inhibitor comprises Ketorolac; the NMDA receptor antagonist comprises Magnesium Sulfate, and the COX inhibitor comprises Ketorolac; the NMDA receptor antagonist comprises Aptiganel, and the COX inhibitor comprises Ketorolac; the NMDA receptor antagonist comprises Ketamine, and the COX inhibitor comprises Acetaminophen; the NMDA receptor antagonist comprises Trilamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine, and the COX inhibitor comprises Parecoxib; the NMDA receptor antagonist comprises Trilamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine, and the COX inhibitor comprises Ibuprofen; the NMDA receptor antagonist comprises Trilamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine, and the COX inhibitor comprises Meloxicam; the NMDA receptor antagonist comprises Tritamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline. and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine, and the COX inhibitor comprises Diclofenac; the NMDA receptor antagonist comprises Trilamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Diclofenac; the NMDA receptor antagonist comprises Minocycline, and the COX inhibitor comprises Diclofenac; the NMDA receptor antagonist comprises Agmatine, and the COX inhibitor comprises Diclofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine, and the COX inhibitor comprises Ketoprofen; the NMDA receptor antagonist comprises Trilamine, and the COX inhibitor comprises Ketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen; the NMDA receptor antagonist comprises Meperidine, and the COX inhibitor comprises Ketoprofen; the NMDA receptor antagonist comprises Minocycline, and the COX inhibitor comprises Ketoprofen; the NMDA receptor antagonist comprises Agmatine, and the COX inhibitor comprises Ketoprofen; the NMDA receptor antagonist comprises Magnesium Sulfate, and the COX inhibitor comprises Ketoprofen; the NMDA receptor antagonist comprises Aptiganel, and the COX inhibitor comprises Ketoprofen; the NMDA receptor antagonist comprises Ketamine, and the COX inhibitor comprises Celecoxib; the NMDA receptor antagonist comprises Trilamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; or the NMDA receptor antagonist comprises Aptiganel, and the COX inhibitor comprises Celecoxib.

Some aspects of the invention comprise at least a local anesthetic comprising cinchocaine, an NMDA receptor antagonist, and a COX inhibitor, which may be packaged as single composition to be marketed as a unit dose, or may be packaged as two, three, or more separate compositions to be combined prior to use, e.g. in the surgical field. In some aspects, the local anesthetic comprises Cinchocaine and: the NMDA receptor antagonist comprises Ketamine, and the COX inhibitor comprises Ketorolac; the NMDA receptor antagonist comprises Trilamine, and the COX inhibitor comprises Ketorolac; the NMDA receptor antagonist comprises Tramadol, and the COX inhibitor comprises Ketorolac; the NMDA receptor antagonist comprises Dextromethorphan, and the COX inhibitor comprises Ketorolac; the NMDA receptor antagonist comprises Meperidine, and the COX inhibitor comprises Ketorolac; the NMDA receptor antagonist comprises Minocydine, and the COX inhibitor comprises Ketorolac; the NMDA receptor antagonist comprises Agmatine, and the COX inhibitor comprises Ketorolac; the NMDA receptor antagonist comprises Magnesium Sulfate, and the COX inhibitor comprises Ketorolac; the NMDA receptor antagonist comprises Aptiganel, and the COX inhibitor comprises Ketorolac; the NMDA receptor antagonist comprises Ketamine, and the COX inhibitor comprises Acetaminophen; the NMDA receptor antagonist comprises Trilamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine, and the COX inhibitor comprises Parecoxib; the NMDA receptor antagonist comprises Trolamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine, and the COX inhibitor comprises Ibuprofen; the NMDA receptor antagonist comprises Trilamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine, and the COX inhibitor comprises Meloxicam; the NMDA receptor antagonist comprises Triamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine, and the COX inhibitor comprises Diclofenac; the NMDA receptor antagonist comprises Trilamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Diclofenac; the NMDA receptor antagonist comprises Minocycline, and the COX inhibitor comprises Diclofenac; the NMDA receptor antagonist comprises Agmatine, and the COX inhibitor comprises Diclofenac; the NMDA receptor antagonist comprises Magnesium Sulfate, and the COX inhibitor comprises Diclofenac; the NMDA receptor antagonist comprises Aptiganel, and the COX inhibitor comprises Didofenac; the NMDA receptor antagonist comprises Ketamine, and the COX inhibitor comprises Ketoprofen; the NMDA receptor antagonist comprises Trilamine, and the COX inhibitor comprises Ketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen; the NMDA receptor antagonist comprises Meperidine, and the COX inhibitor comprises Ketoprofen; the NMDA receptor antagonist comprises Minocycline, and the COX inhibitor comprises Ketoprofen; the NMDA receptor antagonist comprises Agmatine, and the COX inhibitor comprises Ketoprofen; the NMDA receptor antagonist comprises Magnesium Sulfate, and the COX inhibitor comprises Ketoprofen; the NMDA receptor antagonist comprises Aptiganel, and the COX inhibitor comprises Ketoprofen; the NMDA receptor antagonist comprises Trilamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; or the NMDA receptor antagonist comprises Aptiganel, and the COX inhibitor comprises Celecoxib.

Some aspects of the invention comprise at least a local anesthetic comprising Mepivacaine, an NMDA receptor antagonist, and a COX inhibitor, which may be packaged as single composition to be marketed as a unit dose, or may be packaged as two, three, or more separate compositions to be combined prior to use, e.g. in the surgical field. In some aspects, the local anesthetic comprises Mepivacaine and: the NMDA receptor antagonist comprises Ketamine, and the COX inhibitor comprises Ketorolac; the NMDA receptor antagonist comprises Trilamine, and the COX inhibitor comprises Ketorolac; the NMDA receptor antagonist comprises Tramadol, and the COX inhibitor comprises Ketorolac; the NMDA receptor antagonist comprises Dextromethorphan, and the COX inhibitor comprises Ketorolac; the NMDA receptor antagonist comprises Meperidine, and the COX inhibitor comprises Ketorolac; the NMDA receptor antagonist comprises Minocycline, and the COX inhibitor comprises Ketorolac; the NMDA receptor antagonist comprises Agmatine, and the COX inhibitor comprises Ketorolac; the NMDA receptor antagonist comprises Magnesium Sulfate, and the COX inhibitor comprises Ketorolac; the NMDA receptor antagonist comprises Aptiganel, and the COX inhibitor comprises Ketorolac; the NMDA receptor antagonist comprises Ketamine, and the COX inhibitor comprises Acetaminophen; the NMDA receptor antagonist comprises Trilamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine, and the COX inhibitor comprises Parecoxib; the NMDA receptor antagonist comprises Trilamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine, and the COX inhibitor comprises Ibuprofen; the NMDA receptor antagonist comprises Trilamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine, and the COX inhibitor comprises Meloxicam; the NMDA receptor antagonist comprises Trilamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine, and the COX inhibitor comprises Diclofenac; the NMDA receptor antagonist comprises Trilamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Didofenac; the NMDA receptor antagonist comprises Minocydine, and the COX inhibitor comprises Diclofenac; the NMDA receptor antagonist comprises Agmatine, and the COX inhibitor comprises Didofenac; the NMDA receptor antagonist comprises Magnesium Sulfate, and the COX inhibitor comprises Diclofenac; the NMDA receptor antagonist comprises Aptiganel, and the COX inhibitor comprises Didofenac; the NMDA receptor antagonist comprises Ketamine, and the COX inhibitor comprises Ketoprofen; the NMDA receptor antagonist comprises Trilamine, and the COX inhibitor comprises Ketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen; the NMDA receptor antagonist comprises Meperidine, and the COX inhibitor comprises Ketoprofen; the NMDA receptor antagonist comprises Minocycline, and the COX inhibitor comprises Ketoprofen; the NMDA receptor antagonist comprises Agmatine, and the COX inhibitor comprises Ketoprofen; the NMDA receptor antagonist comprises Magnesium Sulfate, and the COX inhibitor comprises Ketoprofen; the NMDA receptor antagonist comprises Aptiganel, and the COX inhibitor comprises Ketoprofen; the NMDA receptor antagonist comprises Ketamine, and the COX inhibitor comprises Celecoxib; the NMDA receptor antagonist comprises Trilamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; or the NMDA receptor antagonist comprises Aptiganel, and the COX inhibitor comprises Celecoxib.

Some aspects of the invention comprise at least a local anesthetic comprising Etidocaine, an NMDA receptor antagonist, and a COX inhibitor, which may be packaged as single composition to be marketed as a unit dose, or may be packaged as two, three, or more separate compositions to be combined prior to use, e.g. in the surgical field. In some aspects, the local anesthetic comprises Etidocaine and: the NMDA receptor antagonist comprises Ketamine, and the COX inhibitor comprises Ketorolac; the NMDA receptor antagonist comprises Trilamine, and the COX inhibitor comprises Ketorolac; the NMDA receptor antagonist comprises Tramadol, and the COX inhibitor comprises Ketorolac; the NMDA receptor antagonist comprises Dextromethorphan, and the COX inhibitor comprises Ketorolac; the NMDA receptor antagonist comprises Meperidine, and the COX inhibitor comprises Ketorolac; the NMDA receptor antagonist comprises Minocycline, and the COX inhibitor comprises Ketorolac; the NMDA receptor antagonist comprises Agmatine, and the COX inhibitor comprises Ketorolac; the NMDA receptor antagonist comprises Magnesium Sulfate, and the COX inhibitor comprises Ketorolac; the NMDA receptor antagonist comprises Aptiganel, and the COX inhibitor comprises Ketorolac; the NMDA receptor antagonist comprises Ketamine, and the COX inhibitor comprises Acetaminophen; the NMDA receptor antagonist comprises Trilamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine, and the COX inhibitor comprises Parecoxib; the NMDA receptor antagonist comprises Trilamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocydine, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine, and the COX inhibitor comprises Ibuprofen; the NMDA receptor antagonist comprises Trilamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine, and the COX inhibitor comprises Meloxicam; the NMDA receptor antagonist comprises Trilamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine, and the COX inhibitor comprises Diclofenac; the NMDA receptor antagonist comprises Trilamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Diclofenac; the NMDA receptor antagonist comprises Minocycline, and the COX inhibitor comprises Diclofenac; the NMDA receptor antagonist comprises Agmatine, and the COX inhibitor comprises Diclofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine, and the COX inhibitor comprises Ketoprofen; the NMDA receptor antagonist comprises Trilamine, and the COX inhibitor comprises Ketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen; the NMDA receptor antagonist comprises Meperidine, and the COX inhibitor comprises Ketoprofen; the NMDA receptor antagonist comprises Minocycline, and the COX inhibitor comprises Ketoprofen; the NMDA receptor antagonist comprises Agmatine, and the COX inhibitor comprises Ketoprofen; the NMDA receptor antagonist comprises Magnesium Sulfate, and the COX inhibitor comprises Ketoprofen; the NMDA receptor antagonist comprises Aptiganel, and the COX inhibitor comprises Ketoprofen; the NMDA receptor antagonist comprises Ketamine, and the COX inhibitor comprises Celecoxib; the NMDA receptor antagonist comprises Trilamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; or the NMDA receptor antagonist comprises Aptiganel, and the COX inhibitor comprises Celecoxib.

Some aspects of the invention comprise at least a local anesthetic comprising Tetracaine, an NMDA receptor antagonist, and a COX inhibitor, which may be packaged as single composition to be marketed as a unit dose, or may be packaged as two, three, or more separate compositions to be combined prior to use, e.g. in the surgical field. In some aspects, the local anesthetic comprises Tetracaine and: the NMDA receptor antagonist comprises Trilamine, and the COX inhibitor comprises Ketorolac; the NMDA receptor antagonist comprises Tramadol, and the COX inhibitor comprises Ketorolac; the NMDA receptor antagonist comprises Dextromethorphan, and the COX inhibitor comprises Ketorolac; the NMDA receptor antagonist comprises Meperidine, and the COX inhibitor comprises Ketorolac; the NMDA receptor antagonist comprises Minocycline, and the COX inhibitor comprises Ketorolac; the NMDA receptor antagonist comprises Agmatine, and the COX inhibitor comprises Ketorolac; the NMDA receptor antagonist comprises Magnesium Sulfate, and the COX inhibitor comprises Ketorolac; the NMDA receptor antagonist comprises Aptiganel, and the COX inhibitor comprises Ketorolac; the NMDA receptor antagonist comprises Ketamine, and the COX inhibitor comprises Acetaminophen; the NMDA receptor antagonist comprises Trilamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine, and the COX inhibitor comprises Parecoxib; the NMDA receptor antagonist comprises Trilamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine, and the COX inhibitor comprises Ibuprofen; the NMDA receptor antagonist comprises Trilamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine, and the COX inhibitor comprises Meloxicam; the NMDA receptor antagonist comprises Trilamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine, and the COX inhibitor comprises Diclofenac; the NMDA receptor antagonist comprises Trilamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Diclofenac; the NMDA receptor antagonist comprises Minocycline, and the COX inhibitor comprises Didofenac; the NMDA receptor antagonist comprises Agmatine, and the COX inhibitor comprises Didofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine, and the COX inhibitor comprises Ketoprofen; the NMDA receptor antagonist comprises Trilamine, and the COX inhibitor comprises Ketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen; the NMDA receptor antagonist comprises Meperidine, and the COX inhibitor comprises Ketoprofen; the NMDA receptor antagonist comprises Minocycline, and the COX inhibitor comprises Ketoprofen; the NMDA receptor antagonist comprises Agmatine, and the COX inhibitor comprises Ketoprofen; the NMDA receptor antagonist comprises Magnesium Sulfate, and the COX inhibitor comprises Ketoprofen; the NMDA receptor antagonist comprises Aptiganel, and the COX inhibitor comprises Ketoprofen; the NMDA receptor antagonist comprises Ketamine, and the COX inhibitor comprises Celecoxib; the NMDA receptor antagonist comprises Trilamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; or the NMDA receptor antagonist comprises Aptiganel, and the COX inhibitor comprises Celecoxib.

In some embodiments, surprisingly and unexpectedly, more than 92% of patients treated with BKK infiltrative formulation for Lumbar Discectomies, Decompressive Lumbar Laminectomies, Anterior Cervical Discectomies and Peripheral Nerve Decompressive Procedure surgeries reported very statistically low to no PONV after 24 hours postoperatively. In one embodiment, 84.8% of patients of the population of patients treated with BKK reported no to mild pain, 13.5% reported moderate pain, with only 1.6% of the population of treated patients reporting severe pain through 24 hours post operatively. Importantly, 100% of patients treated with existing unimodal opioid analgesics for the same surgeries would be predicted to report significant PONV after 24 hours of being treated with prior art anesthetics/analgesics. Notably, the clinical majority of patients treated with prior art analgesic techniques, for the same surgeries, could predictably still suffer noticeable PONV after 3 days of being administered prior art analgesics. As used herein, the term "infiltrative analgesia" means anesthesia/analgesia produced in a local area by injecting an anesthetic/analgesic agent into operative sites or wounds. According to one embodiment, 84.8% of the population of patients treated with the exemplary BKK formulation reported no or mild pain, 13.5% reported moderate pain, and 1.6% reported severe pain 24 hours post operatively. As used and taught herein, the term "infiltrative analgesia" describes analgesia produced in a local area by injecting the analgesic agent into and around operative sites, wounds, incisions, or adjacent fascial planes. Examples of fascial plane blocks include transverse abdominus and erector spinae plane blocks.

As for an example, Shaikh S, et al.[4] reported that in lumbar surgery, like Lumbar Micro-Discectomy, where the anesthetics and analgesics administered intravenously intraoperatively were Propofol 2-2.5 mg·kg-1, Midazolam 1-2 mg, and Fentanyl 1-1.5 µg·kg-1 followed by intravenous Morphine or Ketorolac. Here, Shaikh S. reported an incidence of postoperative nausea of 61% and postoperative vomiting of 9.4%. Most notably, 16% of patients in Shaikh's series suffered severe postoperative nausea and vomiting with a resultant hospital readmission rate of 5.7% due to severe PONV, whereas, only 0.18% patients through 24 hours reported severe PONV in BKK formulation treatment in similar lumbar surgeries with no reported hospital readmission (Table 1 below). Cruthirds D. et al.[5] also demonstrated that after outpatient surgery, the overall incidence of post discharge nausea has been reported to be 17% and of vomiting 8% which was not seen in over 4000 consecutive patients treated with the BKK Formulation through 24 hours postoperatively.

Recently, Patel[6] prior art demonstrated that Ketamine mixed with Bupivacaine as an intrathecal injectable provided better analgesia than Bupivacaine alone. However, the prior art Patel publication cannot be considered as a guideline or teaching to combine Bupivacaine and Ketamine to reduce PONV because Patel further reported that in the 50 patients studied by her, 28% developed PONV in the intrathecal Bupivacaine only group, and 36% developed PONV in the intrathecal Bupivacaine plus Ketamine group. This PONV incidence of Patel as compared to the reported 4000 consecutive neurosurgical cases using Bupivacaine Hydrochloride as the local anesthetic, Ketamine Hydrochloride as the NMDA receptor antagonist, and Ketorolac Tromethamine as the non-competitive COX inhibitor used in an infiltrative block, where surprisingly and unexpectedly, 92.7% of all patients through 24 hours post operatively reported no PONV (Table 1 below). Patel, et al. does not teach or suggest adding the COX inhibitor, Ketorolac in the intrathecal anesthetic/analgesic composition. Patel also reported from other literatures[7,8] that the administration of Ketamine, alone or in combination with other analgesics, is associated with an increased incidence of PONV and other postoperative complications. Therefore, the Patel prior art clearly does not motivate or teach, and in fact, teaches it is counterintuitive to combine Ketamine with Bupivacaine in order to reduce the incidence of PONV at the time the present invention was discovered. Here, the Patel prior art simply teaches away, or in other words, Patel et al. guided interested clinicians in an opposite direction from the direction where the present invention proceeded. Table 1 summarizes this discussion and the unexpected surprising results.

Clearly, one of ordinary skill would not be able to make a projection from Patel that the combination of Bupivacaine, Ketamine, and Ketorolac at a concentration of 0.01% to 0.4%, 0.2 to 3 mg/ml, and 0.01 to 1.2 mg/ml, respectively, would result in an anesthetic/analgesic that provides a clinically important and statistically significant reduction in postoperative PONV, in which surprisingly and unexpectedly, 92.7% of over 4000 consecutive patients reported no PONV, 0% reported mild PONV, 5.37% reported moderate PONV, and 0.18% reported severe PONV through 24 hours post operatively.

In some embodiments, the local anesthetic comprises Bupivacaine Hydrochloride. In some embodiments, the local anesthetic comprises Lidocaine, Ropivacaine, Levobupivacaine, Prilocaine, Amethocaine, Procaine, Cinchocaine, Mepivacaine, Etidocaine, or any other long acting local anesthetic. In some embodiments, the NMDA receptor antagonist comprises Ketamine, Trilamine, Meperidine, Tramadol, or any other phencyclidine NMDA antagonist or derivative. In some embodiments, the COX inhibitor comprises Ketorolac, Acetaminophen, Parecoxib, Diclofenac, Ibuprofen, Meloxicam, or any other parenteral COX inhibitor drug in this class.

It is well documented in the literature that postoperative pain can have a significant impact on patient recovery, patient safety and experience. Apfelbaum, J. et al.[9] reported of the approximately 73,000,000 surgeries performed in the United States each year, 80% of those patients experience postoperative pain from the immediate postoperative period until 2 weeks after discharge. Of those patients studied by Apfelbaum, 86% reported moderate, severe, or extreme pain and 25% of those patients who received standard of care unimodal opioid-based analgesia reported an opioid adverse drug effect, many times PONV. Gan T. J, et al[10] interviewed 300 patients having surgery within the previous five years finding, 86% experienced pain after surgery, and of these, 75% reported moderate to extreme pain immediately post-operation, with 74% experiencing pain after discharge. Therefore, there is an urgent and until the present invention, unmet clinical need to develop an improved opioid free analgesic formulation to significantly reduce postoperative pain and postoperative nausea and vomiting for patients undergoing painful surgeries or painful procedures.

The opioid-free formulation of the present invention allows for a non-addictive simple and effective alternative to

TABLE 1

PONV (nausea & vomiting for the first 24-48 hours post-surgery)

| Formulation | % of patients with NO PONV | % of patients with SEVERE PONV | Reference | Conclusion |
| --- | --- | --- | --- | --- |
| BKK | >92% | 0.18% | Present invention | Dramatic and superior reduction in PONV for BKK |
| Propofol, Midazolam, and Fentanyl at induction followed by intravenous Morphine or Ketorolac as additional analgesia | 30% | 16% | Shaikh et al. | Higher incidence of PONV |
| Bupivacaine + Saline | 72% | No data | Patel et al. | Presence of Ketamine increases PONV. In contrast, BKK surprisingly reduced PONV. |
| Bupivacaine + Ketamine | 64% | No data | | | pain management without the morbidity of PONV. This approach is especially critical to help prevent opioid addiction and overdose that may result from using opioids for the approximate tens of millions of inpatient and outpatient procedures performed annually in the US and contributing to the current opioid crisis. As of October 2017, the US Government declared the opioid pandemic a public health emergency. Opioid overdoses claimed over 64,000 lives in 2017 alone. In the US a patient dies due to opioid overdose every 4 minutes. There are over 53 million inpatient and 57 million outpatient procedures performed in the US annually and the majority are exposed to opioids. The Council of Economic Advisors estimated the true cost of the opioid pandemic in 2015 to be 504.0 billion dollars, or 2.8% of GDP. Therefore, the current invention provides an opioid-free analgesic/anesthetic allowing for a "non-addictive", much needed innovation, in order to treat acute pain and avoid or eliminate an initial or repeated opioid exposure.

In some embodiments, the present invention discloses an opioid-free anesthetic/analgesic formulation comprising Bupivacaine Hydrochloride, Ketamine Hydrochloride, and Ketorolac Tromethamine (hereinafter "BKK Formulation") at a concentration of 0.01% to 0.5%, 0.2 to 3 mg/ml and 0.01 to 1.2 mg/ml, respectively which is effective to significantly reduce postoperative pain as compared to existing prior art anesthetic/analgesic compositions.

in some embodiments, the concentration of Bupivacaine, Ropivacaine, or Levobupivacaine is about 0.125%. In some embodiments, the concentration of Bupivacaine, Ropivacaine, or Levobupivacaine is between about 0.01% to 0.05%. In some embodiments, the concentration of Bupivacaine, Ropivacaine, or Levobupivacaine is between about 0.025% to 0.075%. In some embodiments, the concentration of Bupivacaine, Ropivacaine, or Levobupivacaine is between about 0.05% to 0.1%. In some embodiments, the concentration of Bupivacaine, Ropivacaine, or Levobupivacaine is between about 0.05% to 0.125%. In some embodiments, the concentration of Bupivacaine, Ropivacaine, or Levobupivacaine is between about 0.1% to 0.15%. In some embodiments, the concentration of Bupivacaine, Ropivacaine, or Levobupivacaine is between about 0.1% to 0.2%. In some embodiments, the concentration of Bupivacaine, Ropivacaine, or Levobupivacaine is between about 0.125% to 0.2%. In some embodiments, the concentration of Bupivacaine, Ropivacaine, or Levobupivacaine is between about 0.15% to 0.25%. In some embodiments, the concentration of Bupivacaine, Ropivacaine, or Levobupivacaine is between about 0.2% to 0.3%. In some embodiments, the concentration of Bupivacaine, Ropivacaine, or Levobupivacaine is between about 0.3% to 0.4%. In some embodiments, the concentration of Bupivacaine, Ropivacaine, or Levobupivacaine is more than about 0.4% to 0.5%.

In some embodiments, the concentration of Ketamine Tromethamine is about 1 mg/ml. In some embodiments, the concentration of Ketamine is between about 0.1 to 0.5 mg/ml. In some embodiments, the concentration of Ketamine is between about 0.5 to 1.0 mg/ml. In some embodiments, the concentration of Ketamine is between about 0.5 to 1.5 mg/ml. In some embodiments, the concentration of Ketamine is between about 1 to 2 mg/ml. In some embodiments, the concentration of Ketamine is between about 1 to 3 mg/ml. In some embodiments, the concentration of Ketamine is more than 3 mg/ml and may exceed 10 mg/mi. In some embodiments the concentration of another substituted NMDA receptor antagonist will be similar to the Ketamine concentration or any other NMDA receptor antagonist concentration providing effective analgesia.

In some embodiments, the concentration of Ketorolac Tromethamine is about 0.2 mg/ml. In some embodiments, the concentration of Ketorolac is between about 0.01 to 1.0 mg/mi. In some embodiments, the concentration of Ketorolac is between about 0.05 to 0.95 mg/mi. In some embodiments, the concentration of Ketorolac is between about 0.15 to 0.95 mg/ml. In some embodiments, the concentration of Ketorolac is between about 0.1 to 0.2 mg/ml. In some embodiments, the concentration of Ketorolac is between about 0.2 to 0.3 mg/ml. In some embodiments, the concentration of Ketorolac about 0.3 to 1.0 mg/ml. In some embodiments the concentration of Ketorolac is greater than 1 mg/ml. In some embodiments the substituted cyclooxygenase inhibitor concentration will be similar or identical to the Ketorolac concentration or any other cyclooxygenase inhibitor concentration providing effective analgesia.

According to some embodiments, surprisingly, more than 25% of postoperative neurosurgical patients treated with the intraoperative BKK infiltrative formulation for Lumbar Discectomies, Decompressive Lumbar Laminectomies, Anterior Cervical Discectomies with Fusion and Peripheral Nerve Decompressive surgeries reported NO PAIN through 24 hours in 4000 consecutive neurosurgical cases. Among these same 4000 consecutive neurosurgical cases, through 24 hours postoperatively, 25.40% reported no pain, 59.4% patients reported mild pain, 13.5% patients reported moderate pain, and only 1.6% reported severe pain. The discovery that opioid-free multimodal BKK is an effective multimodal anesthetic/analgesic that abolishes pain completely in more than 25% of 4000 consecutive neurosurgical procedures and permit severe pain in only 1.6% of neurosurgeries through 24 hours post-surgery is surprising and unexpected because there is nothing in the reported and published medical and scientific literature that suggests or teaches the combination of the three ingredients from three different drug classes, would return this statistically significant and surprising result.

Recently, the Wang prior art[11] disclosed that sixty-two patients undergoing total hip arthroplasty with spinal anesthesia were treated with either 13.5 mg hyperbaric Bupivacaine with Normal Saline or 13.5 mg hyperbaric Bupivacaine with 2 mg preservative-free Ketorolac. The results suggest that the pain during the first 2 days after surgery did not differ between the Ketorolac and Saline groups, importantly the postoperative opioid use did not differ between the Ketorolac and Saline groups (Table 2 below). Wang reported the presence and area of hyperalgesia and allodynia surrounding the wound objectively measured at 48 h postoperatively was similar from each differently treated group. Therefore, this peer-reviewed and published literature demonstrated inefficiency and lack of clinical efficacy of Ketorolac to reduce postoperative pain, when it is combined with Bupivacaine, as compared to Bupivacaine alone, clearly teaching that a motivation is lacking, it would be counter-intuitive, to combine Ketorolac and Bupivacaine at the time the present invention was discovered. The Wang prior art is also pointing researchers in an opposite direction than the direction of the present invention. In other words, Wang et. al. teaches away from the proposed combination of Bupivacaine, Ketamine and Ketorolac as a multimodal analgesic composition, as claimed in the present invention, in order to significantly reduce postoperative pain.

In another literature, Rahmanian et al.[12] disclosed the clinical ineffectiveness of Local Infiltrative Bupivacaine in Lumbar Laminectomy. Rahmanian reported that 30 mL of 0.25% Bupivacaine Hydrochloride administered as an infiltrative field block at the time of surgical closure was no more effective than 30 ml Normal Saline in decreasing postoperative surgical pain. Pain was assessed at rest using subjective linear VAS scores. In the Rahmanian prior art, VAS scores in the Bupivacaine group were surprisingly more than the control Normal Saline group (Table 2 below). The Rahmanian reported findings, compared to those reported using BKK infiltration in the exact same surgical procedure, where BKK was used as an infiltrative anesthetic/analgesic in thousands of surgeries, are disruptive and provide contrary teaching, guiding the student of the art away from the current invention. Table 2 summarizes this discussion.

TABLE 2

PAIN RELIEF ROST OPERATIVELY AFTER PAINFUL PROCEDURES

| Formulation | Patients with NO PAIN | Patients with MILD PAIN | Time | Reference | Conclusion |
|---|---|---|---|---|---|
| BKK | 25.4% | 59.4% | 24 hr | Present Invention | The BKK formulation shows a surprising result to reduce postoperative pain. |
| Bupivacaine + Ketorolac intrathecal and intravenous morphine or hydromorphone with subsequent oral oxycodone 24 hr. Postoperative. | 0% | 0% | 24 hr | Wang et al. | Bupivacaine + Ketorolac combination intrathecal is not more effective than Bupivacaine + Saline intrathecal combination in reducing post-operative pain. |
| Bupivacaine Infiltrative Block | 0% | 0% | 12 hr. | Rahmanian et al. | 30 mL of 0.25% Bupivacaine Hydrochloride was no more effective than 30 ml Normal Saline in decreasing postoperative surgical pain. |
| Saline Infiltrative Block | 0% | 0% | | | |

Clearly, one of ordinary skill would not be able to make a projection from Wang and/or Rahmanian, that the combination of Bupivacaine Hydrochloride, Ketamine Hydrochloride, and Ketorolac Tromethamine at a concentration of 0.01% to 0.4%; 0.2 to 3 mg/ml, and 0.01 to 1.2 mg/ml, respectively, would result in an anesthetic/analgesic that surprisingly allows NO pain in more than 25% of patients, mild pain in 59.4%, moderate pain in 13.5% and severe pain in only 1.6% of the BKK treated patients 24 hours postoperatively. Wang and Rahmanian published peer reviewed and reported findings that are disruptive and contradictory to using the BKK formulation of the present invention in the exact same surgical procedure. The exemplary BKK formulation clearly provides a clinically and statistically significant improvement compared to standard of care that is counterintuitive to existing standard of care therapies.

In some embodiments, the BKK formulation further comprises a saline solution. In some embodiments, Bupivacaine Hydrochloride is added to the saline solution at a desired concentration. In some embodiments, Ketorolac Tromethamine and Ketamine Hydrochloride is added to the Bupivacaine Hydrochloride and saline solution.

As a non-limiting example, an opioid-free, antiemetic multimodal analgesic formulation may comprise 0.25% Bupivacaine Hydrochloride with 1:400,000 epinephrine, 1.0 mg/ml Ketorolac Tromethamine, and 1 mg/ml of Ketamine Hydrochloride.

The following is a non-limiting example of preparing the analgesic formulation in a 60 cc syringe containing 0.25% Bupivacaine Hydrochloride with 1:400,000 epinephrine, 1.0 mg/ml Ketorolac Tromethamine, and 1 mg/ml of Ketamine Hydrochloride:

1. Following USP 797/800 guidelines, Dilute 30 ml of 0.5% Bupivacaine Hydrochloride, epinephrine 1:200,000, into 27.4 cc preservative free Normal Saline (NS);
2. Add 2.0 ml of Ketorolac Tromethamine 30 mg/cc;
3. Add 0.6 ml of Ketamine Hydrochloride 100 mg/cc.

In some embodiments, the BKK formulation is administered between about every 3 to 6 hours until the pain completely subsides. In some embodiments, for clinical purposes, the volume of the BKK formulation used as a single infiltration may vary from between about 0.1 mL to 1000 mL.

In some embodiments, the formulation further comprises a Transient Potential Vanilloid (TRPV) Receptor agonist or antagonist. In some embodiments, the TRVP agonist is Capsaicin or Resiniferatoxin, or any other agonist. In some embodiments, the TRVP antagonist is Capazepine or any other aryl urea cinnamide, or caroxamide antagonist, the TRPV receptor agonist or antagonist in a dose of 400 micrograms to 10,000 micrograms in 60 to 120 cc of an acceptable vehicle. In some embodiments, the formulation further comprises a protein kinase inhibitor at a concentration of 0.001 mg/cc to 0.1 mg/cc. In some embodiments, the protein kinase inhibitor is Timsirolimus. In some embodiments, the formulation further comprises a competitive or non-competitive glycine or glutamate antagonist. Non-limiting examples of the competitive or non-competitive glycine or glutamate antagonist are Magnesium Sulfate, Ramacemide, and Tiletamine at a concentration of 0.001 mg/cc to 0.1 mg/cc.

In some embodiments, the formulation further comprises Acetaminophen or Paracetamol, or other parental cyclooxygenase type 3 inhibitor at doses of 1 mg/cc to 20 mg/cc. In some embodiments, the formulation contains an alpha 2 agonist. Non-limiting examples of alpha 2 agonists include, but are not limited to, Clonidine, Dexmedetomidine, Tizanidine, Guanfacine, and Medetomidine. In some instances, the concentration of the alpha 2 agonist is 0.008 mg/cc to 0.001 mg/cc. In some embodiments the formulation contains a steroid. Non-limiting examples of steroids include but are not limited to, Dexamethasone, Methylprednisolone, Betamethasone Propionate, Betamethasone Sodium Phosphate, or another anti-inflammatory mineralocorticosteroid or glucocorticosteroid in concentrations of 0.1 mg/cc to 1 mg/cc.

In some embodiments, the BKK formulation has an increased shelf life as compared to the shelf lives of the individual components of the formulation. In some embodiments, the BKK formulation comprises a buffer for enhancing shelf life. In some embodiments, the formulation comprises a buffer for raising or lowering the pKa of the formulation. Buffers are used to control a pH of a formulation by preventing pronounced variations in pH during use or storage. Preferably, the buffers may buffer the formulation from a pH of about 7.3 to a pH of about 7.6, more preferably from a pH of about 7.35 to a pH of about 7.5, and most preferably from a pH of about 7.3 to a pH of about 7.4. Non-limiting examples of buffers include citric acid, triethanolamine, acetates, and phosphates. By inhibiting inflammation at the infiltration site, the anti-inflammatory actions of the BKK components favorably improve the pharmacokinetics of the BKK at the site of surgical inflammation adding to improved efficacy of the amide local anesthetic component.

In some embodiments, the BKK formulation further comprises epinephrine. In some embodiments, a concentration of epinephrine is between about 1:200,000 to 1:800,000. In some embodiments, the BKK formulation further contains and comprises a beta-lactam antibiotic. In some embodiments, the BKK formulation further contains Vancomycin. In some embodiments, the BKK formulation contains an antifibrinolytic, Tranexamic Acid or other drug or compound in this class.

Without wishing to limit the present invention to any theory or mechanism, it is believed that the BKK formulation of the present invention has a bactericidal and/or a bacteriostatic effect.

In some embodiments, the BKK formulation of the present invention is used as a preemptive analgesic. Preemptive analgesics are administered prior to the onset of nociceptive stimulus as a means to prevent or reduce subsequent pain.

In some embodiments, the BKK formulation is administered at or adjacent to the sites of nociception to provide preventative pain relief. In some embodiments, the BKK formulation is administered once a day, for example, for fast, temporary pain relief or more frequently, such as twice or three times a day, to maintain pain relief. BKK formulation used as a single infiltration may vary from between about 10 to 1000 mL. In some embodiments, the volume of the BKK formulation used as a single infiltration may vary from between about 100 to 1000 mL. In some embodiments, the volume of the BKK formulation used as a single infiltration may vary from between about 500 to 1000 mL. In some embodiments, the volume of the BKK formulation used as a single infiltration may vary from between about 0.1 to 100 mL. In some embodiments, the volume of the BKK formulation used as a single infiltration may vary from between about 0.1 to 10 mL. The BKK formulation may be delivered to the surgical site by single injections or thru infiltration catheters strategically placed prior to surgery, or at surgical wound closure, allowing the formulation to be delivered to the surgical site or fascial plane containing nerves that innervate the surgical site.

The volume of the formulation may depend on a patient's weight and the required effective minimal concentration of the formulation. In one embodiment, the required effective minimal concentration of the BKK formulation components is 0.048 to 0.5% of the local anesthetic, 0.12 mg/kg to 1 mg/kg of the N-methyl-D-aspartate (NMDA) receptor antagonist, and 0.4 mg/kg to 1.2 mg/kg of the cyclooxygenase (COX) inhibitor. As a non-limiting example, a patient weighing 160 pounds, or 72.7 kgs, and having a lumbar spinal procedure may safely be administered 60 mL of the exemplary concentrations of BKK; 0.25% Bupivacaine with or without epinephrine, 1 mg/cc Ketorolac, and 1 mg/cc Ketamine.

In some embodiments, the BKK formulation may be delivered as a continuous infusion for delivering the formulation to targeted muscle and soft tissue including skin, subcutaneous tissue and fat, fascial planes, bone, and peripheral sensory nerves. In some embodiments, continuous infusion rates of the formulation vary from 1.0 mL to 100 mL per hour. In some embodiments, continuous infusion rates of the formulation vary from 1.0 mL to 10 mL per hour. In some embodiments, continuous infusion rates of the formulation vary from 10 mL to 50 mL per hour. In some embodiments, continuous infusion rates of the formulation vary from 50 mL to 100 mL per hour. In some embodiments, the formulation is administered intradermally, intranasally, rectally, trans dermally or subcutaneously, using, for example, a needle and syringe or catheter.

In some embodiments, the BKK formulation is used at any location in the body where pain reduction is required or desirable. In some embodiments, the BKK formulation is used to treat pain, other than neuropathic pain. This would apply to pain caused by injuries, such as wounds and burns, and at/in facilities where medical procedures, dental procedures, veterinary procedures, and cosmetic procedures are performed. For example, the BKK formulation may be administered to a patient having an abrasion, cut, puncture wound, incision, or other skin or soft tissue wound that causes pain. As another example, burns also cause pain and administering the BKK formulation would rapidly reduce the pain.

In other embodiments, the present invention further features a method for treating post-surgical pain in a patient in need thereof comprising administering to the patient a therapeutically effective amount of a neurokinin-1 (NK-1) receptor antagonist in combination with a pain medication. In some embodiments, the post-surgical pain is not neuropathic pain. In preferred embodiments, the NK-1 receptor antagonist is selected from a group consisting of aprepitant, rolapitant, netupitant, lanepitant, vestipitant, orvepitant maleate, casopitant, ezlopitant, sertopitant, fosaprepitant, befetupitant, maropitant, or a pharmaceutically acceptable salt thereof. For example, the NK-1 receptor antagonist may be aprepitant. Dose ranges of the NK-1 receptor antagonist may range from 0.001 mg/kg to 25 mg/kg per day. In other embodiments, two or more neurokinin-1 (NK-1) receptor antagonists may be combined and administered to the patient. For example, aprepitant may optionally be combined with vestipitant and casopitant. Aprepitant may included in the formulation in a dosage range of about 0.05 mg to about 750 mg. When vestipitant is included in the formulation, it is provided in a dosage range of about 0.001 mg to about 200 mg. Alternatively or in conjunction, when casopitant is included in the formulation, it is provided in a dosage range of about 0.005 mg to about 1,000 mg.

In preferred embodiments, the pain medication used in combination with the NK-1 receptor antagonist may be selected from local anesthetics, opioids, non-steroid anti-inflammatory drug (NSAID), anticonvulsants, serotonin and norepinephrine reuptake inhibitors (SNRIs), acetaminophen, and tricyclic antidepressants.

The following is a non-limiting example of administering said formulation to a patient requiring surgery, for example, decompressive lumbar laminectomy with fusion:

Preoperative Period

1. The patient is injected at or near the surgical site with 5 to 60 cc's of the BKK formulation 1 hour prior to the surgical procedure. The injection may be guided using anatomic landmarks, ultrasound, or x-ray.

Interoperative Period

2. The patient is injected with 5 to 120 cc of the BKK formulation as an infiltrative field block or fascial plane block prior to surgery, or at the time of wound closure.

Postoperative Period

3. The patient is administered a continuous infusion of the BKK formulation delivered through a catheter system incorporated into the tissue adjacent to the surgical incision or adjacent fascial plane. For example, an erector spinae plane block with a continuous infusion via direct placement of strategically localized and anatomically placed catheters.

In some embodiments, the BKK formulation is utilized in veterinary applications. In some embodiments, the formulation is administered to animals such as dogs, cats, horses, rabbits, or other mammals. In some embodiments, the BKK formulation is utilized in dental applications. For example, in order to relieve the pain from an extraction, the BKK formulation may be injected to a patient's gums prior to or after extracting a tooth or performing dental procedures providing multimodal opioid free anti-emetic analgesia.

In alternative embodiments, the present exemplary admixture formulation may be interchanged with another parenteral analgesic drug as a substituted drug class component, in a similar or identical concentration, and having a similar or identical mechanism of action.

As used herein, the term "about" refers to plus or minus 10% of the referenced number.

Various modifications of the invention, in addition to those described herein, will be apparent to those skilled in the art from the foregoing description. For example, reference to USPTO US2009/0093669 A1 may be applied to enable the invention to allow active transdermal delivery. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the FIGURES presented in this patent application are drawn to scale, including the angles, ratios of dimensions, etc. In some embodiments, the figures are representative only and the claims are not limited by the dimensions of the FIGURES. In some embodiments, descriptions of the inventions described herein using the phrase "comprising" includes embodiments that could be described as "consisting essentially of" or "consisting of," and as such the written description requirement for claiming one or more embodiments of the present invention using the phrase "consisting of" is met.

REFERENCES

1. Sébastien P. et al. Continuing Education In Anesthesia Critical Care and Pain 2013, 13 (1), 28-32.
2. Gan T. J. et al. Anesthesia Analgesia 2014; 118:85-113.
3. Koivuranta M. et al. Anesthesia, 1997, 443-449.
4. Shaikh S. et al. Canadian Journal of Anesthesia 2003, 50(5), 514-518.
5. Cruthirds D. et at. Oral Surgery Oral Medicine Oral Pathology Oral Radiology 2013, 115(5), 601-611.
6. Patel I. et al. National Journal of Medical Research, 2011, 1(2), 71-75.
7. Bjon J. F. et al. Anesthesia, 1984, 39(10), 1023-1028.
8. Kathirvel S. et al. Anesthesia, 2000, 55(9), 899-904.
9. Apfelbaum, J. et al. Anesthesia Analgesia, 2003, 97:534-40.
10. Gan T. J, et al. Current. Medical. Research and Opinion. 2014, 30(1), 149-160.
11. Wang L. et. al. Journal of Anesthesia 2014 28:790-793.
12. Rahmanian A. et al Neurosurgery Quarterly 2014: Nov. 6, 1-5.

What is claimed:

1. A method of treating pain, said method comprising administering, by subcutaneous injection, intramuscular injection, intrafascial injection, or intradermal injection, an effective amount of a formulation to a mammal in need of such treatment, the formulation comprising about 0.01%-0.5% of a local anesthetic comprising bupivacaine or ropivacaine, about 0.01-3.0 mg/cc of an N-methyl-D-aspartate (NMDA) receptor antagonist comprising $MgSO_4$ or ketamine, and about 0.01-1.2 mg/cc of a cyclooxygenase (COX) inhibitor comprising meloxicam or ketorolac.

2. The method of claim 1, wherein the formulation further comprises an alpha agonist, a steroid, a Transient Receptor Potential channel agonist or antagonist, a beta-lactam antibiotic, a protein kinase inhibitor, a competitive or non-competitive glycine or glutamate antagonist, a glutamate or glycine inhibitor, a cyclooxygenase 3 inhibitor, vancomycin, tranexamic acid, or combinations thereof.

3. The method of claim 1, wherein the formulation further comprises a Transient Receptor Potential Vanilloid (TRPV) receptor agonist or antagonist, acetaminophen, paracetamol, dexamethasone, a corticosteroid, cephazolin, vancomycin, tranexamic acid, or a combination thereof.

4. The method of claim 1, wherein the local anesthetic comprises Ropivacaine Hydrochloride.

5. The method of claim 1, wherein the NMDA receptor antagonist comprises Magnesium Sulfate.

6. The method of claim 1, wherein the COX inhibitor comprises Meloxicam.

7. The method of claim 1, wherein the formulation is administered via a pump or a syringe.

8. The method of claim 1, wherein the formulation is administered to a site prior to a needle insertion, an incision, or other medical, veterinarian or dental procedure.

9. The method of claim 1, wherein the formulation is administered in a single injection to the subject.

10. The method of claim 1, wherein the formulation is administered as a continuous infusion rate of about 0.1 mL to 100 mL per hour to the subject.

11. The method of claim 1, wherein the formulation comprises about 0.01%-0.5% of ropivacaine, about 0.01-3.0 mg/cc of $MgSO_4$, and about 0.01-1.2 mg/cc of meloxicam.

12. The method of claim 11, further comprising administering an alpha agonist to the mammal.

13. The method of claim 12, wherein the alpha agonist is epinephrine.

14. The method of claim 1, wherein the formulation comprises about 0.01%-0.5% of bupivacaine, about 0.01-3.0 mg/cc of ketamine, and about 0.01-1.2 mg/cc of ketorolac.

15. The method of claim 14, further comprising administering an alpha agonist to the mammal.

16. The method of claim 15, wherein the alpha agonist is epinephrine.

\* \* \* \* \*